United States Patent
Tano et al.

(10) Patent No.: US 9,623,212 B2
(45) Date of Patent: Apr. 18, 2017

(54) GUIDE WIRE

(71) Applicant: TERUMO KABUSHIKI KAISHA, Shibuya-ku (JP)

(72) Inventors: Yutaka Tano, Fujinomiya (JP); Yousuke Nabeshima, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 2 days.

(21) Appl. No.: 14/338,681

(22) Filed: Jul. 23, 2014

(65) Prior Publication Data
US 2014/0336594 A1  Nov. 13, 2014

Related U.S. Application Data

(63) Continuation of application No. PCT/JP2013/052338, filed on Feb. 1, 2013.

(30) Foreign Application Priority Data

Feb. 7, 2012  (JP) ................................ 2012-024353
Feb. 7, 2012  (JP) ................................ 2012-024354

(51) Int. Cl.
*A61B 5/00* (2006.01)
*A61M 25/00* (2006.01)
*A61M 25/09* (2006.01)

(52) U.S. Cl.
CPC ..... *A61M 25/09* (2013.01); *A61M 2025/0915* (2013.01); *A61M 2025/09066* (2013.01);
(Continued)

(58) Field of Classification Search
CPC ........ A61M 25/09; A61M 2025/09133; A61M 2025/09175; A61L 31/10; C08L 27/18; C08L 83/04
(Continued)

(56) References Cited

U.S. PATENT DOCUMENTS 5,885,227 A * 3/1999 Finlayson ............. A61M 25/09
                                                       600/585
6,656,134 B2 * 12/2003 Reynolds ................ A61L 31/10
                                                       600/585
(Continued)

FOREIGN PATENT DOCUMENTS

JP   2005-185376 A   7/2005
JP   2008-307367 A  12/2008
(Continued)

OTHER PUBLICATIONS

International Search Report (PCT/ISA/210) mailed on Apr. 23, 2013, by the Japanese Patent Office as the International Searching Authority for International Application No. PCT/JP2013/052338.

*Primary Examiner* — Devin Henson
(74) *Attorney, Agent, or Firm* — Buchanan Ingersoll & Rooney PC

(57) ABSTRACT

A guide wire includes an elongated wire body having flexibility; a distal member that covers a distal portion of the wire body and is configured to have a resin material; and a hydrophilic lubricant layer that is formed so as to cover a proximal end of the distal member and is configured to have a hydrophilic material. In addition, the hydrophilic lubricant layer has a tapered shape whose outer diameter gradually decreases toward a proximal side. In addition, the maximum outer diameter of the hydrophilic lubricant layer is smaller than the maximum outer diameter of the distal member. In addition, a proximal portion of the distal member has a tapered shape whose outer diameter gradually decreases toward the proximal side, and a distal end of the hydrophilic lubricant layer is positioned at the tapered portion of the distal member.

8 Claims, 10 Drawing Sheets

(52) U.S. Cl.
CPC ............ *A61M 2025/09091* (2013.01); *A61M 2025/09133* (2013.01); *A61M 2025/09175* (2013.01)

(58) Field of Classification Search
USPC .......................................................... 600/585
See application file for complete search history.

(56) References Cited

U.S. PATENT DOCUMENTS

| | | | |
|---|---|---|---|
| 8,376,962 B2 | 2/2013 | Kousai et al. | |
| 2003/0229298 A1* | 12/2003 | Iwami ................... | A61M 25/09 600/585 |
| 2007/0293791 A1* | 12/2007 | Lee ......................... | A61L 31/10 600/585 |
| 2008/0161728 A1* | 7/2008 | Mishima ............... | A61M 25/09 600/585 |
| 2008/0281230 A1* | 11/2008 | Kinoshita ............. | A61M 25/09 600/585 |
| 2009/0054921 A1 | 2/2009 | Yanuma | |
| 2010/0004561 A1 | 1/2010 | Nabeshima | |
| 2010/0228229 A1* | 9/2010 | Kousai ................... | A61L 31/10 604/528 |
| 2013/0006222 A1 | 1/2013 | Nabeshima et al. | |

FOREIGN PATENT DOCUMENTS

| | | |
|---|---|---|
| JP | 2009-045464 A | 3/2009 |
| JP | 2010-011883 A | 1/2010 |
| JP | 2010-207348 A | 9/2010 |
| JP | 2010-239981 A | 10/2010 |
| WO | WO 2011/118443 A1 | 9/2011 |

* cited by examiner

GUIDE WIRE

CROSS REFERENCES TO RELATED APPLICATIONS

This application is a continuation of International Application No. PCT/JP2013/052338 filed on Feb. 1, 2013, and claims priority to Japanese Application Nos. 2012-024353 filed on Feb. 7, 2012 and 2012-024354 filed Feb. 7, 2012, the entire content all of which is incorporated herein by reference.

TECHNICAL FIELD

The disclosure here relates to a guide wire.

BACKGROUND DISCUSSION

When inserting a catheter into a living body lumen such as a digestive tract and a blood vessel, a guide wire is used in order to guide the catheter to a target site of the living body lumen. The guide wire is used by being inserted into the catheter. In addition, observation or treatment of the living body lumen is also performed by using an endoscope, and thus the guide wire is used in order to guide the catheter inserted into the endoscope or a lumen of the endoscope to the target site of the living body lumen.

A guide wire is known which has an elongated wire body, a resin coating layer for covering a distal portion of the wire body and an annular member arranged on a proximal side of the resin coating layer. Such a conventional guide wire has a problem, however, in that when a distal portion of the guide wire is curved with a comparatively small radius of curvature, the proximal end of the resin coating layer and the distal end of the annular member may be separated from each other, thus producing a crack in the boundary between them. Specifically, the proximal portion of the resin coating layer may peel away from the wire body and may turn up. Thus, when the catheter is pushed in along the guide wire from a proximal end of the guide wire, a distal end of the catheter may be caught on the turned-up part of the guide wire.

Guide wires disclosed in JP-A-2008-307367 and WO 2011/118443, for example, prevent turning up of the resin coating layer by defining a proximal outer diameter of the resin coating layer and a distal outer diameter of the annular member. It has been found however that further modifications are required to prevent turning up of the guide wire and thereby improve operability.

SUMMARY

The disclosure herein provides a guide wire which can reliably prevent a medical device such as a catheter used in combination with the guide wire from being caught on a turned-up portion of the guide wire when a proximal side portion of a coating layer thereof is turned up.

An exemplary embodiment of a guide wire according to the disclosure here includes an elongated wire body having flexibility; a distal member that covers a distal portion of the wire body and is configured to have a resin material; and a hydrophilic lubricant layer that is formed so as to cover a proximal end of the distal member and is configured to have a hydrophilic material.

In a further aspect of the exemplary embodiment of the guide wire, at least a proximal portion of the hydrophilic lubricant layer has a tapered shape whose outer diameter gradually decreases toward a proximal side.

In a still further aspect of the exemplary embodiment of the guide wire, the maximum outer diameter of the hydrophilic lubricant layer is smaller than the maximum outer diameter of the distal member.

Still further, the exemplary embodiment of the guide wire according to the disclosure here includes a cylindrical member that is inserted onto the wire body and whose distal portion is positioned at a proximal portion of the distal member, in which an outer surface of the cylindrical member is formed to have unevenness, and the outer surface of the cylindrical member is coated with the hydrophilic lubricant layer.

In a further aspect of the exemplary embodiment of the guide wire, a plurality of concave portions is formed on the outer surface of the cylindrical member, and the unevenness is formed by the plurality of concave portions.

In a further aspect of the exemplary embodiment of the guide wire, the concave portion is formed to have a melting portion which is concavely deformed to the wire body side by melting a portion of the cylindrical member.

In addition, according to a further aspect of the exemplary embodiment of the guide wire, the hydrophilic lubricant layer is inserted into the concave portion.

In a further aspect of the exemplary embodiment of the guide wire, the proximal portion of the distal member has a tapered shape in which an outer diameter thereof gradually decreases toward the proximal side and in which a distal of the hydrophilic lubricant layer is positioned at the tapered portion of the distal member.

In yet a further aspect of the exemplary embodiment of the guide wire, the wire body has a first constant outer diameter portion which is positioned at the distal side and whose outer diameter is constant in a longitudinal direction, a second constant outer diameter portion which is positioned at a further proximal side than the first constant outer diameter portion and whose outer diameter is larger than the outer diameter of the first constant outer diameter portion and is constant in the longitudinal direction, and a tapered portion which is positioned between the first constant outer diameter portion and the second constant outer diameter portion and whose outer diameter gradually decreases toward the distal side, and in which the proximal of the distal member is positioned at the second constant outer diameter portion.

In a further aspect of the exemplary embodiment of the guide wire, the resin material is mainly a urethane resin.

According to the exemplary embodiment of the guide wire disclosed herein, when continuously pushing a medical device such as a catheter used in combination with a guide wire (referred to as a "catheter" as a representative example) to a target site of a living body lumen along the guide wire toward a distal direction, a distal end of the catheter slides on a hydrophilic lubricant layer and is finally contacted with the middle of a distal member. When the catheter is moved as described above, even if external force is applied to a proximal end of the distal member by the distal end of the catheter, the proximal end of the distal member is covered with the hydrophilic lubricant layer and is likely to slide on a proximal surface. Therefore, the force applied by the catheter is dissipated and thus a proximal end of the distal member does not evolve into the turned-up portion mentioned above. Accordingly, it is possible to reliably prevent the proximal end of the distal member from being turned up by the distal end of the catheter being caught thereon.

In particular, when an outer surface of a cylindrical member is covered with the hydrophilic lubricant layer and the outer surface of the cylindrical member is formed to have unevenness, the hydrophilic lubricant layer is inserted into the unevenness, thereby improving adhesion of the hydrophilic lubricant layer to the cylindrical member. Therefore, it is possible to prevent or suppress peeling of the hydrophilic lubricant layer from the cylindrical member.

DETAILED DESCRIPTION

Hereinafter, a guide wire of the disclosure herein will be described in detail with reference to preferred exemplary embodiments illustrated in the accompanying drawings.

First Embodiment

Figure 1:
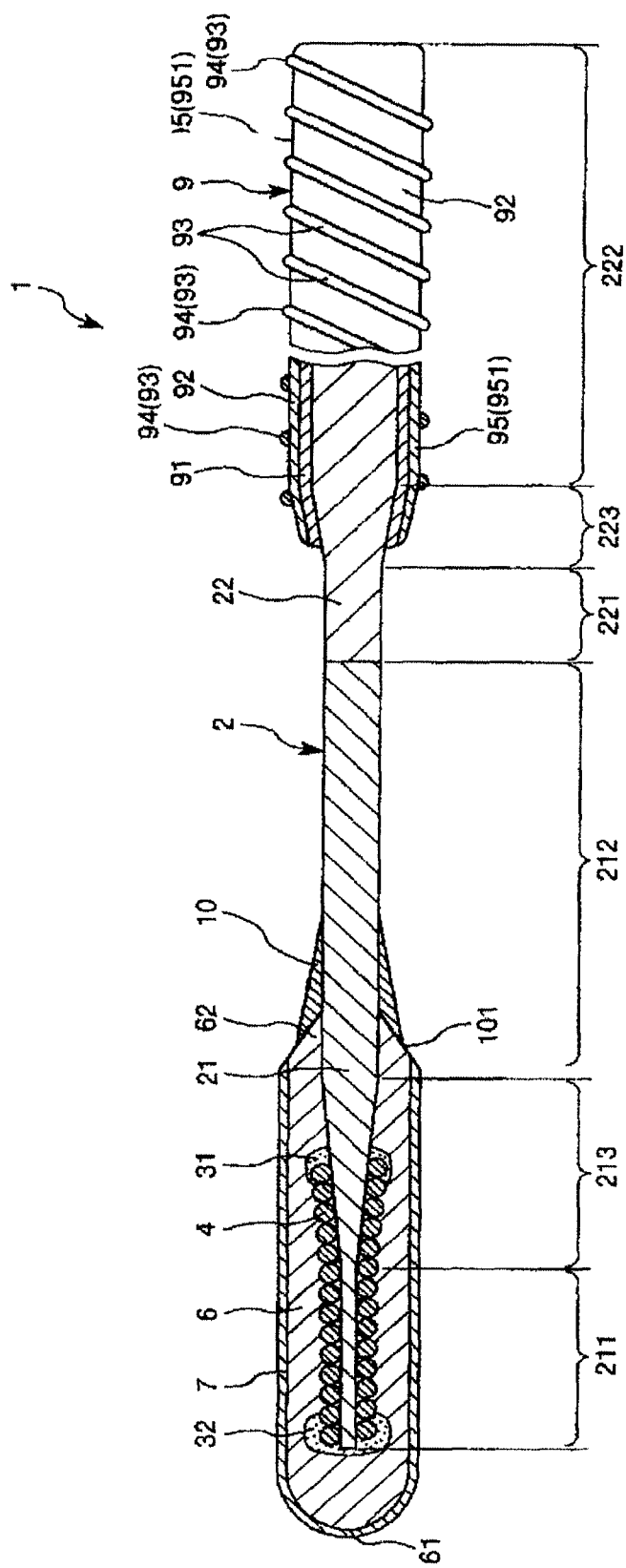
FIG. 1 is a vertical cross-sectional view illustrating a first exemplary embodiment of a guide wire of the disclosure.
Figure 2:
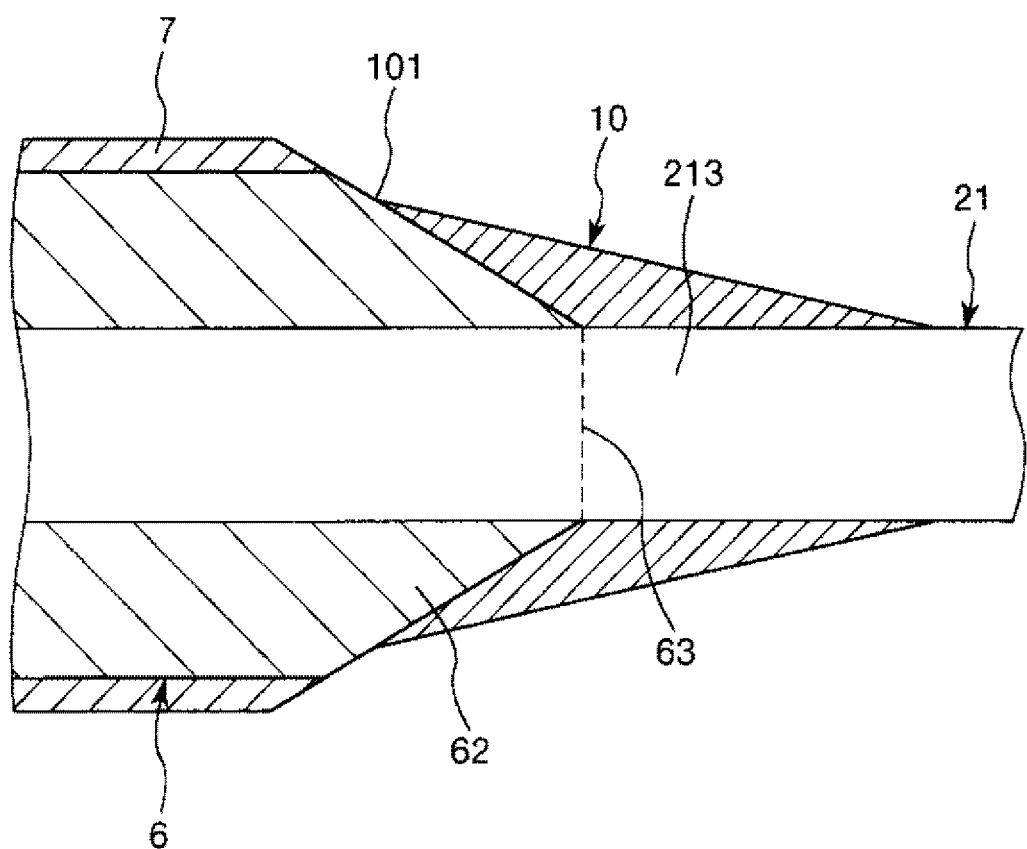
FIG. 2 is an enlarged cross-sectional view of a protruding portion included in the guide wire illustrated in FIG. 1.
Figure 3:
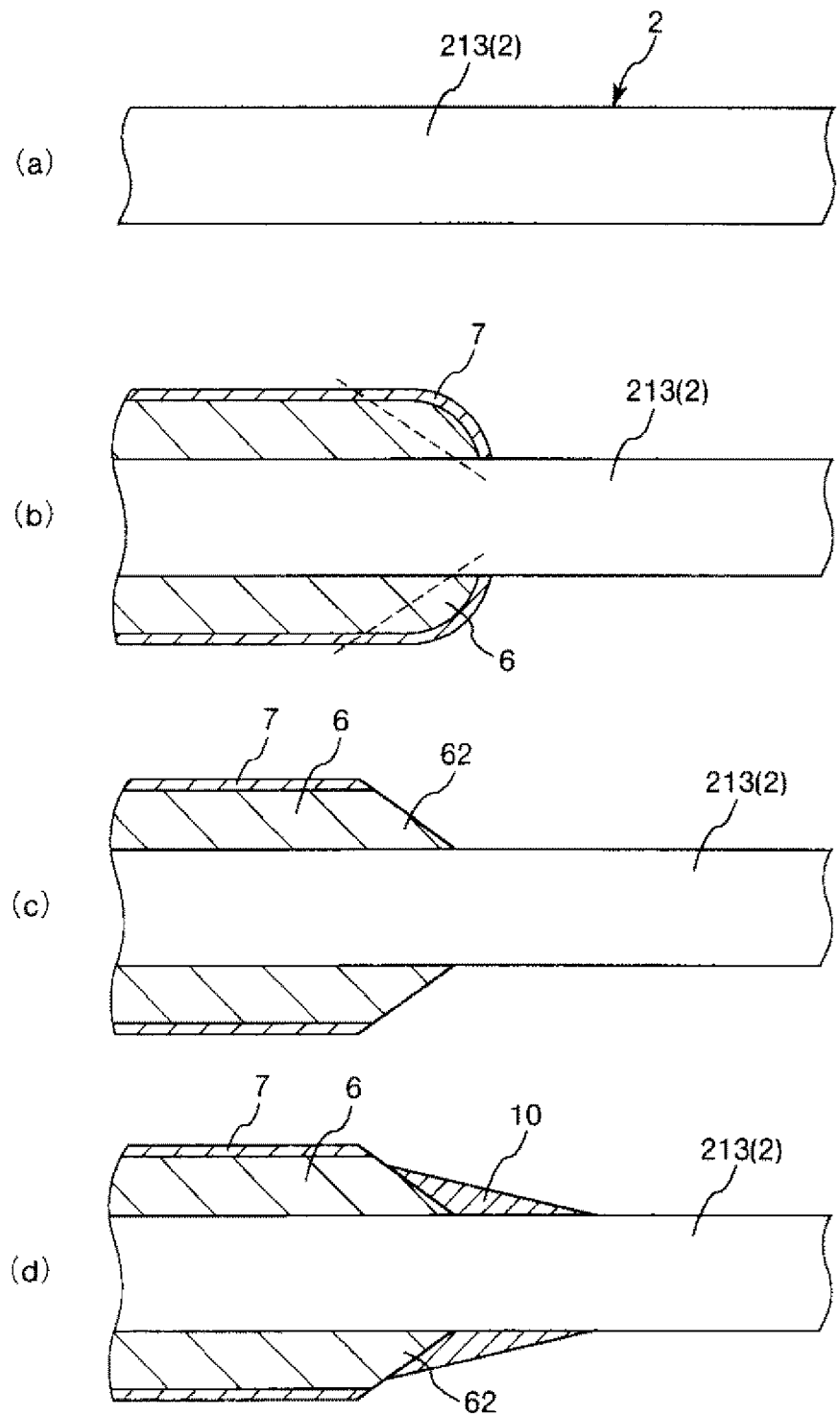
FIG. 3 is a cross-sectional view illustrating an example of a manufacturing method of the guide wire illustrated in FIG. 1.

FIG. 1 is a vertical cross-sectional view illustrating a first exemplary embodiment of a guide wire of the disclosure here, FIG. 2 is an enlarged cross-sectional view of a protruding portion included in the guide wire illustrated in FIG. 1, and FIG. 3 is a cross-sectional view illustrating an example of a manufacturing method of the guide wire illustrated in FIG. 1.

Hereinafter, for convenience of description, a right side in FIG. 1 (similarly applied to FIGS. 2 and 3 which will be described later) is referred to as a "proximal", and a left side in FIG. 1 is referred to as a "distal". In addition, in each drawing, in order to facilitate understanding, the guide wire is schematically illustrated in such a manner that the guide wire is shortened in a longitudinal direction and is excessively extended in a thickness direction, respectively. A ratio of dimensions in the longitudinal direction to dimensions in the thickness direction is different from the actual ratio.

A guide wire 1 illustrated in FIGS. 1 to 3 is a catheter guide wire used by being inserted into a lumen of a catheter (also including an endoscope). The guide wire 1 as described above has an elongated wire body 2, a spiral coil 4, a distal member 6, a distal side coating layer 7, a hydrophilic lubricant layer 10 and a coating layer 9.

An overall length of the guide wire 1 is not particularly limited, but it is preferable that the overall length be approximately 200 mm to 5,000 mm. In addition, an average outer diameter of the guide wire 1 is not particularly limited, but it is preferable that the average outer diameter be approximately 0.2 mm to 1.2 mm.

As illustrated in FIG. 1, the wire body 2 is configured to have a first wire 21 arranged at the distal side and a second wire 22 arranged at the proximal side of the first wire 21. The first wire 21 and the second wire 22 are firmly connected to each other by welding.

A welding method between the first wire 21 and the second wire 22 is not particularly limited. For example, the welding method includes spot welding using a laser, butt resistance welding such as butt seam welding, and the like. However, it is preferable to use the butt resistance welding.

The first wire 21 is a wire having elasticity. A length of the first wire 21 is not particularly limited, but it is preferable that the length be approximately 20 mm to 1,000 mm.

In the exemplary embodiment, the first wire 21 has a first constant outer diameter portion 211 and a second constant outer diameter portion 212 which are positioned at both end portions thereof and whose outer diameters are constant in the longitudinal direction, and a tapered portion (first gradually decreasing outer diameter portion) 213 which is positioned between the first constant outer diameter portion 211 and the second constant outer diameter portion 212 and whose diameter gradually decreases toward a distal direction. The outer diameter of the second constant outer diameter portion 212 is configured to be larger than the outer diameter of the first constant outer diameter portion 211.

By thus positioning the tapered portion 213, it is possible to gradually decrease rigidity (flexural rigidity, torsional rigidity) of the first wire 21 toward the distal direction. As a result, the guide wire 1 obtains excellent flexibility in the distal portion, thereby improving its ability to follow blood vessels and safety. In addition, it is also possible to prevent the guide wire 1 from being bent.

The length of the tapered portion 213 is not particularly limited, but it is preferable that the length be approximately 10 mm to 1,000 mm, and it is more preferable that the length be approximately 20 mm to 300 mm. If the length falls within this range, it is possible to more gradually change the rigidity along the longitudinal direction.

In the exemplary embodiment, the tapered portion 213 has a tapered shape whose outer diameter continuously decreases toward the distal direction at a substantially constant decreasing rate. In other words, a tapering angle of the tapered portion 213 is substantially constant along the longitudinal direction. This enables the guide wire 1 to be gradually changed in the rigidity along the longitudinal direction.

Further, as an alternative to the above-described configuration, the tapering angle of the tapered portion 213 may be changed along the longitudinal direction. For example, the tapered portion 213 may be formed by alternately repeating a relatively large tapering angle portion and a relatively small tapering angle portion multiple times. In this case, some portions of the tapered portion 213 may be formed so that the tapering angle is zero degrees.

It is preferable that a structural material of the first wire 21 be a metal material. For example, it is possible to use various metal materials such as stainless steel (for example, SUS304, SUS303, SUS316, SUS316L, SUS316J1, SUS316J1L, SUS405, SUS430, SUS434, SUS444, SUS429, SUS430F, SUS302, and the like) and pseudo-elastic alloys (including super-elastic alloy). However, it is preferable to use a super-elastic alloy. The super-elastic alloy is relatively flexible, resilient, and is unlikely to be curled. By configuring the first wire 21 to have a super-elastic alloy, the guide wire 1 can obtain sufficient flexibility and resilience against bending of a distal side portion thereof. Thus, it is possible to obtain better operability by improving its ability to follow blood vessels which are complicatedly curved and bent. Even if the first wire 21 is repeatedly curved and bent, the first wire 21 is unlikely to be curled due to its resilience. Therefore, it is possible to prevent degraded operability which would be caused if the first wire 21 was likely to be curled when the guide wire 1 is used.

The pseudo-elastic alloy includes all of those which have any shape of a stress-strain curve caused by tension, those which can significantly measure a transformation point of As, Af, Ms, Mf or the like, those which cannot measure the transformation point, and those which are largely deformed by stress and restore their own shape by removing the stress.

A preferred composition of the super-elastic alloy includes Ni—Ti alloys such as Ni—Ti alloys containing Ni in a range of 49 wt % to 52 wt %, Cu—Zn alloys containing Zn in a range of 38.5 wt % to 41.5 wt %, Cu—Zn—X alloys containing X in a range of 1 wt % to 10 wt % (X is at least one type among Be, Si, Sn, Al and Ga), Ni—Al alloys containing Al in a range of 36 wt % to 38 wt %, and the like. Among these, a particularly preferred composition is the aforesaid Ni—Ti alloy.

The distal portion of the second wire 22 is connected with the proximal portion of the first wire 21. The second wire 22 is a wire having elasticity. The length of the second wire 22 is not particularly limited, but it is preferable that the length be approximately 20 mm to 4,800 mm.

In the exemplary embodiment, the second wire 22 has constant outer diameter portions 221 and 222 which are positioned at both end portions thereof and whose outer diameters are constant in the longitudinal direction, and a tapered portion (second gradually decreasing outer diameter portion) 223 which is positioned between the constant outer diameter portions 221 and 222 and whose outer diameter gradually decreases toward the distal direction. Preferably, the outer diameter of the constant outer diameter portion 221 is substantially equal to the outer diameter of the second constant outer diameter portion 212 of the first wire 21.

By positioning the tapered portion 223 in the second wire 22 in this manner, it is possible to gradually decrease rigidity (flexural rigidity, torsional rigidity) of the second wire 22 toward the distal direction. As a result, operability and safety are improved when the guide wire 1 is inserted into a living body.

In the exemplary embodiment, the tapered portion 223 has a tapered shape whose outer diameter continuously decreases toward the distal direction at a substantially constant decreasing rate. In other words, a tapering angle of the tapered portion 223 is substantially constant along the longitudinal direction. This enables the rigidity of the guide wire 1 to be gradually changed along the longitudinal direction.

Unlike in the above-described exemplary configuration, the tapering angle of the tapered portion 223 may also be changed along the longitudinal direction. For example, the tapered portion 223 may be formed by alternately repeating a relatively large tapering angle portion and a relatively small tapering angle portion multiple times. In this case, some portions of the tapered portion 223 may be formed so that the tapering angle is zero degree.

It is preferable that a structural material of the second wire 22 be a metal material. It is possible to use various metal materials such as stainless steel (for example, all types of SUS such as SUS304, SUS303, SUS316, SUS316L, SUS316J1, SUS316J1L, SUS405, SUS430, SUS434, SUS444, SUS429, SUS430F, SUS302, and the like), a piano wire, cobalt-based alloys, and pseudo-elastic alloys.

Among these, the cobalt-based alloy has a high elastic modulus when formed into the wire, and an appropriate elastic limit. Therefore, the second wire 22 constructed from the cobalt-based alloy has a particularly good torque transmission capability, and thus the problem of buckling is extremely unlikely to occur. As long as the cobalt-based alloys contain Co as an element thereof, any one may be used. However, it is preferable to use those which contain Co as a main ingredient (i.e., in a Co-based alloy, the Co content rate is the highest in view of a weight ratio). It is more preferable to use Co—Ni—Cr-based alloys. The alloy of the above-described composition has plasticity even in deformation at room temperature. Accordingly, for example, it is possible to easily deform the alloy into a desired shape when in use. In addition, the alloy of the above-described composition has a high elastic modulus and can be subjected to cold forming with a high elastic limit. Since the alloy has a high elastic limit, it is possible to miniaturize the guide wire 1 while sufficiently preventing the buckling from occurring. Therefore, it is possible for the guide wire 1 to have sufficient flexibility and rigidity to allow it to be inserted into a desired site.

In addition, when stainless steel is used as the structural material of the second wire 22, the guide wire 1 can obtain better thrust-in performance and torque transmission capability.

In the guide wire 1, the first wire 21 and the second wire 22 may also be formed from an alloy of the same type as each other. The alloy may be the pseudo-elastic alloy, and for example, may include Ni—Ti-based alloys.

Further, in the guide wire 1, the first wire 21 and the second wire 22 may be formed from alloys which are different types from each other. In this case, it is preferable that the first wire 21 be constructed from a material having an elastic modulus lower than that of the second wire 22. This allows the guide wire 1 to have excellent flexibility in the distal side portion and to have sufficient rigidity (flexural rigidity, torsional rigidity) in the proximal side portion. As a result, the guide wire 1 obtains excellent thrust-in performance and torque transmission capability. While ensuring good operability, the guide wire 1 obtains good flexibility and resilience in the distal side. In this regard, an ability to follow blood vessels and safety are improved.

In addition to the above-described combination, it is preferable that the first wire 21 be formed from the super-elastic alloy (Ni—Ti alloy) and the second wire 22 be formed from stainless steel. This allows the above-described effects to be more prominent.

The coil 4 is arranged to extend around an outer periphery of the distal portion of the wire body 2. The coil 4 is a member formed by winding element wires in a spiral shape and covers the outer periphery of the distal portion of the wire body 2. The wire body 2 is inserted through a substantially central portion inside the coil 4. In the guide wire 1, the coil 4 is in contact with the wire body 2, that is, is in close contact with the outer periphery of the wire body 2. However, without being limited thereto, for example, the coil 4 may be separated from the outer periphery of the wire body 2.

In addition, in the guide wire 1, in a state without receiving external force, the coil 4 preferably has no gap between the element wires wound in the spiral shape. However, in the state without receiving the external force, the coil 4 may have a gap between the element wires wound in the spiral shape, unlike in the exemplary illustration.

It is preferable that the coil 4 be configured to have an X-ray opaque metal material (material having an X-ray contrast property). For example, the material includes precious metals such as gold, platinum, tungsten and the like, or alloys containing these (for example, platinum-iridium alloy). Since the coil 4 is configured to have an X-ray opaque metal material, the guide wire 1 has an X-ray contrast property. Preferably, it is possible to insert the guide wire 1 into the living body while checking a position of the distal portion in X-ray fluoroscopy.

The proximal portion of the coil 4 is fixed to the tapered portion 213 of the wire body 2 via a fixing material 31, and the distal portion of the coil 4 is fixed to the first constant outer diameter portion 211 of the wire body 2 via a fixing material 32. The fixing materials 31 and 32 are respectively configured to have solder (brazing material) or various adhesives.

In addition, the guide wire 1 has the distal member 6 which collectively covers the distal portion of the wire body 2, the coil 4 and the fixing materials 31 and 32. The distal member 6 is in close contact with the outer periphery of the distal portion of the wire body 2. Note that, in the exemplary embodiment as illustrated, the distal member 6 is not inserted into the coil 4, but it may alternatively be inserted into the coil 4.

The distal member 6 can be formed for various purposes. As an example thereof, it is possible to dispose the distal member 6 in order to improve an operability of the guide wire 1 by enhancing a sliding property and to improve safety when inserting the guide wire 1 into the blood vessels.

A distal surface 61 of the distal member 6 is rounded. This enables the distal surface 61 to prevent damage to an endothelial wall of a body cavity such as blood vessels.

In addition, the proximal portion of the distal member 6 is configured to have a tapered portion 62 whose outer diameter gradually decreases toward the proximal side.

Further, a proximal end 63 of the distal member 6 is positioned at the second constant outer diameter portion 212 of the first wire 21. In this manner, the proximal end 63 of the distal member 6 is positioned at the second constant outer diameter portion 212 whose outer diameter is the largest within the first wire 21 and whose rigidity is high. Accordingly, when the guide wire 1 is curved for example, it is possible to effectively prevent turning up starting from the first wire 21 of the proximal portion of the distal member 6. Note that, as will be described later, the turning-up of the proximal portion of the distal member 6 is prevented by the hydrophilic lubricant layer 10. However, if the proximal end 63 of the distal member 6 is positioned as described above, a synergistic effect with the hydrophilic lubricant layer 10 allows the above-described effects to be more prominent. Note that, the proximal end 63 may be positioned in the tapered portion 62.

The distal member 6 is configured to have a sufficiently flexible material (soft material, elastic material). The material is not particularly limited, but for example, includes a polyolefin such as a polyethylene, a polypropylene and the like, a polyvinyl chloride, a polyester (PET, PBT and the like), a polyamide, a polyimide, a polyurethane, a polystyrene, a polycarbonate, a silicone resin, a fluorine resin (PTFE, ETFE, PFA and the like), or composite materials thereof, various rubber materials such as a latex rubber, a silicone rubber and the like, or composite materials obtained by combining two or more out of these materials. In particular, it is preferable to use a urethane-based resin out of these materials. If the distal member 6 is mainly configured to have the urethane-based resin, the flexibility in the distal portion of the guide wire 1 is further improved. Therefore, when inserting the guide wire 1 into the blood vessels, it is possible to reliably prevent damage to the endothelial wall inside the blood vessels, thereby extremely improving safety.

In addition, particles (filler) composed of the X-ray opaque material may be dispersed in the above-described distal member 6. In this case, the guide wire 1 achieves an X-ray contrast property. Therefore, it is possible to insert the guide wire 1 into the living body while checking a position of the distal portion in X-ray fluoroscopy. The X-ray opaque material is not particularly limited, but for example, includes precious metals such as platinum, tungsten and the like, or an alloy material containing these materials.

A thickness of the distal member 6 is not particularly limited, but may be appropriately selected in view of forming purposes, a material thereof and a forming method of the distal member 6. In general, the average thickness is preferably approximately 5 µm to 500 µm, and more preferably approximately 10 µm to 350 µm. Note that, the distal member 6 may be a laminated body having two or more layers.

A distal side coating layer 7 is formed so as to cover an external surface of the aforementioned distal member 6. The distal side coating layer 7 is configured from a material which can reduce frictional resistance (sliding resistance) with the endothelial wall in the blood vessels or an inner wall of catheter. The material is not particularly limited, but for example, includes hydrophilic materials such as cellulosic polymeric materials, polyethylene oxide polymeric materials, maleic anhydride-based polymeric materials (for example, a maleic anhydride copolymer such as a methyl vinyl ether-maleic anhydride copolymer), acrylamide polymeric materials (for example, a block copolymer of a polyacrylamide, a polyglycidyl methacrylate-dimethyl acrylamide (PGMA-DMAA)), a water-soluble nylon, a polyvinyl alcohol, a polyvinyl pyrrolidone, and the like.

In many cases, the hydrophilic material shows lubricity by being wet (absorbed), and reduces the frictional resistance (sliding resistance) with the endothelial wall in the blood vessels or the inner wall of catheter. This improves the sliding property of the guide wire 1 with respect to the endothelial wall in the blood vessels or the inner wall of catheter. Accordingly, the operability of the guide wire 1 inside the blood vessels or the catheter becomes more excellent.

The distal side coating layer 7 covers only the distal side of the distal member 6. That is, the tapered portion 62 of the distal member 6 is not covered with the distal side coating layer 7, but is exposed, without the distal side coating layer 7. In this manner, without forming the distal side coating layer 7 in the tapered portion 62, it is possible to form the hydrophilic lubricant layer 10 by bringing it into contact with the external surface of the distal member 6. Therefore, it is possible to improve adhesion between the hydrophilic lubricant layer 10 and the distal member 6, and thus it is possible to increase the strength of the hydrophilic lubricant layer 10.

The hydrophilic lubricant layer 10 is formed so as to cover the proximal end 63 of the aforementioned distal member 6. That is, the hydrophilic lubricant layer 10 is formed in a region including the proximal end 63, the distal side and the proximal side thereof. In this manner, the hydrophilic lubricant layer 10 covers the proximal end 63 of the distal member 6 so as to prevent the peeling of the proximal portion of the distal member 6 from the wire body 2. Furthermore, the distal portion of the catheter which is moved from the proximal side is prevented from coming into contact with the proximal end 63. Therefore, with the hydrophilic lubricant layer 10 being so disposed, it is possible to prevent the distal portion of the distal member 6 from being turned up and the catheter from being caught thereon. Accordingly, it is possible to obtain the guide wire 1 which exhibits excellent operability. Specifically, even if the moved distal portion of the catheter applies external force to the proximal end 63 of the distal member 6, the proximal end 63 of the distal member 6 is covered with the hydrophilic lubricant layer 10 and is likely to slide on the surface of the proximal end 63. Accordingly, the force applied by the catheter dissipates and thus the proximal end 63 of the distal member 6 does not become turned-up. Therefore, the proximal end 63 of the distal member 6 is reliably prevented from being turned up due to the caught distal portion of the catheter.

In particular, the hydrophilic lubricant layer 10 directly coats the proximal end 63 of the distal member 6 and smoothly extends further so as to directly coat the surface of the wire body 2. In this manner, even if the distal portion of the catheter slides on the surface of the wire body 2, it is possible to prevent turning up by having the hydrophilic lubricant layer 10 continuously disposed from the wire body 2 to the proximal end 63 of the distal member 6.

In the hydrophilic lubricant layer 10, a distal portion 101 thereof is positioned in the middle of the tapered portion 62 of the distal member 6. As described above, the tapered portion 62 is a portion exposed from the distal side coating layer 7. By positioning the distal portion 101 of the hydrophilic lubricant layer 10 in this portion, it is possible to improve adhesion of the distal portion of the hydrophilic lubricant layer 10.

In addition, it is preferable that the maximum outer diameter of the hydrophilic lubricant layer 10 (that is, the outer diameter of the distal portion 101) be smaller than the outer diameter (maximum diameter) of the distal member 6. This can prevent the hydrophilic lubricant layer 10 from excessively protruding. For example, excessive contact between the hydrophilic lubricant layer 10 and the endothelial wall of the blood vessels is suppressed. Therefore, it is possible to prevent the operability from being degraded. Note that, the aforementioned "outer diameter of the hydrophilic lubricant layer 10" means the outer diameter in a wet (swollen) state.

The hydrophilic lubricant layer 10 has a tapered shape whose outer diameter gradually decreases toward the proximal side. This can smoothly guide the catheter moved from the proximal side to the distal side along the surface of the hydrophilic lubricant layer 10. It is preferable that the tapering angle of the hydrophilic lubricant layer 10 be smaller than the tapering angle of the tapered portion 62 of the distal member 6 so as to more smoothly guide the aforementioned catheter to the distal side.

In this exemplary embodiment, an entire region in the longitudinal direction of the hydrophilic lubricant layer 10 has a tapered shape. However, for example only, the distal portion or the proximal portion may be configured to partially have the tapered shape. In addition, the tapering angle of the hydrophilic lubricant layer 10 may be changed along the longitudinal direction. For example, the tapering angle may be configured so as to gradually increase toward the distal side.

In addition, the length of the hydrophilic lubricant layer 10 is not particularly limited, but it is preferable that the length be approximately 0.5 mm to 2 mm. By adopting the above mentioned length, it is possible to set a sufficient length which enables the hydrophilic lubricant layer 10 to perform its function and can effectively prevent both an increase in the manufacturing cost of the guide wire 1 which is caused by an excessively lengthened hydrophilic lubricant layer 10 and the degradation of the operability.

The hydrophilic lubricant layer 10 is configured to have a hydrophilic material. For example, the hydrophilic material may include cellulosic polymeric materials, polyethylene oxide polymeric materials, maleic anhydride-based polymeric materials (for example, a maleic anhydride copolymer such as a methyl vinyl ether-maleic anhydride copolymer), acrylamide polymeric materials (for example, a block copolymer of a polyacrylamide and a polyglycidyl methacrylate-dimethyl acrylamide (PGMA-DMAA)), a water-soluble nylon, a polyvinyl alcohol, a polyvinyl pyrrolidone, and the like.

In many cases, the hydrophilic material shows lubricity by being wet (absorbed), and reduces the frictional resistance (sliding resistance) with the endothelial wall in the blood vessels or the inner wall of the catheter. This improves the sliding property of the guide wire 1 with respect to the endothelial wall in the blood vessels or the inner wall of the catheter. Accordingly, the operability of the guide wire 1 inside the blood vessels or the catheter is improved.

The coating layer 9 is formed so as to cover the proximal portion of the wire body 2, specifically, substantially an entire region from the proximal portion of the second wire to the tapered portion 223. The coating layer 9 is configured so that an inner layer 91, an outer layer 92 and a linear body 93 are formed (stacked) around the outer periphery of the wire body 2 in this order.

The inner layer 91 is formed on the outer periphery of the wire body 2. The resin material of the inner layer 91 is not particularly limited, but it is preferable to use a fluorine-based resin material, for example. In addition, the inner layer 91 preferably contains two types of fluorine-based resin material whose compositions are different from each other. For example, as two types of fluorine-based resin material, it is possible to use polytetrafluoroethylene (PTFE) for one type and fluoride ethylene propylene (FEP) for the other type.

Furthermore, since the inner layer 91 is formed on the outer periphery of the wire body 2, in order to improve the adhesion to the wire body 2, the inner layer 91 contains a resin material functioning as a binder in the materials of the inner layer 91. The resin material is not particularly limited, but for example, includes a polysulfone, a polyimide, a polyether ether ketone, a polyarylene ketone, a polyphenylene sulfide, a polyarylene sulfide, a polyamide-imide, a polyether-imide, a polyimide sulfone, a polyarylsulfone, a polyaryether sulfone, a polyester, a polyether sulfone, and the like.

The thickness of the inner layer 91 is not particularly limited, but for example, it is preferable that the thickness be 0.001 mm to 0.020 mm. It is more preferable that the thickness be 0.001 mm to 0.010 mm.

The outer layer 92 is formed on the inner layer 91. The resin material of the outer layer 92 is not particularly limited, but for example, it is preferable to use a fluorine-based resin material similar to that of the inner layer 91. As the fluorine-based resin material, for example, it is possible to use polytetrafluoroethylene (PTFE), fluoride ethylene propylene (FEP) and the like.

The thickness of the outer layer 92 is also not particularly limited, but for example, it is preferable that the thickness be 0.001 mm to 0.030 mm. It is more preferable that the thickness be 0.001 mm to 0.015 mm.

The linear body 93 is formed on the outer layer 92. The linear body 93 is wound in a spiral shape (refer to FIG. 1). In this manner, the linear body 93 is disposed around substantially an entire periphery of the second wire 22. In addition, the linear body 93 is coarsely wound so that the adjacent wires are separate from each other. In the exemplary embodiment, the number of formed linear bodies 93 is one or more. When the number of formed linear bodies 93 is two or more, the spiral winding directions of the respective linear bodies 93 may be the same as each other, or may be opposite to each other.

The arrangement of the linear body 93 allows the second wire 22 (wire body 2) to have a plurality of convex portions 94 formed by the linear body 93 on the outer surface thereof and a plurality of concave portions 95 formed between the adjacent convex portions 94 (linear bodies 93).

The resin material in the linear body 93 is not particularly limited, but for example, it is preferable to use a fluorine-based resin material similar to that of the inner layer 91. As the fluorine-based resin material, for example, it is possible to use polytetrafluoroethylene (PTFE), fluoride ethylene propylene (FEP) and the like.

In the guide wire 1, the frictional coefficient of the convex portion 94 (linear body 93) is preferably smaller than the frictional coefficient of a bottom 951 (exposed portion of the outer layer 92) of the concave portion 95.

An exemplary manufacturing method of the guide wire 1 will be briefly described below.

First, the wire body 2 having the first wire 21 and the second wire 22 joined together by welding is prepared by fixing the coil 4 to the wire body 2 using the fixing materials 31 and 32. Note that, in FIG. 3(a), the second wire 22, the coil 4 and the fixing materials 31 and 32 are not illustrated.

Next, as illustrated in FIG. 3(b), the distal member 6 configured to have the resin material such as urethane is formed in the distal portion of the first wire 21, and the distal side coating layer 7 configured to have the hydrophilic material is further formed thereon so as to cover the external surface of the distal member 6. Note that, as illustrated in the drawing, in this stage, the tapered portion 62 is not formed in the distal member 6, and the entire region of the external surface of the distal member 6 is covered with the distal side coating layer 7.

Next, as illustrated in FIG. 3(c), an unnecessary portion is removed by using a file, for example. The proximal side of the distal member 6 and the distal side coating layer 7 are formed in a tapered shape. In this manner, the tapered portion 62 is formed and exposed from the distal side coating layer 7. At this time, the external surface of the tapered portion 62 of the distal member 6 is roughened by the file. Therefore, it is possible to further improve the adhesion of the hydrophilic lubricant layer 10 which is to be formed in the subsequent process.

Next, the hydrophilic lubricant layer 10 configured to have a hydrophilic material is formed so as to cover the proximal end 63 of the distal member 6.

Then, although not illustrated, the guide wire 1 is obtained by forming the coating layer 9 on the wire body 2.

A second exemplary embodiment of a guide wire of the disclosure will be described below.

Figure 4:
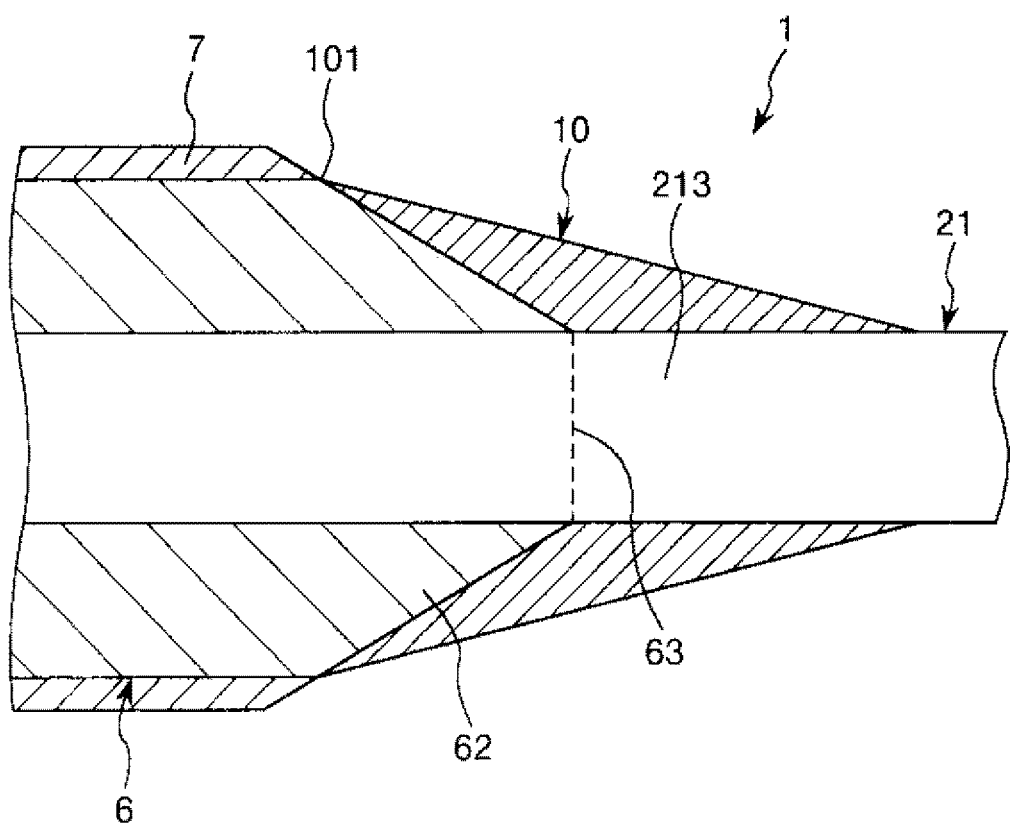
FIG. 4 is a partially enlarged vertical cross-sectional view illustrating a second exemplary embodiment of a guide wire of the disclosure.

FIG. 4 is a partially enlarged vertical cross-sectional view illustrating the second exemplary embodiment of the guide wire of the disclosure.

Hereinafter, the guide wire of the second exemplary embodiment will be described. However, points different from those of the guide wire in the first exemplary embodiment will be mainly described. The same points will not be described.

The guide wire of this exemplary embodiment is the same as the guide wire of the first exemplary embodiment except that the configurations of the hydrophilic lubricant layer are different from each other.

As illustrated in FIG. 4, in this exemplary embodiment, the distal end 101 of the hydrophilic lubricant layer 10 is positioned at the distal end of the tapered portion 62 of the distal member 6. That is, the distal end 101 of the hydrophilic lubricant layer 10 is positioned at a boundary between the outwardly exposed distal member 6 and the distal side coating layer 7. The tapered portion 62 is a portion exposed from the distal side coating layer 7. Accordingly, it is possible to improve the adhesion of the hydrophilic lubricant layer 10 to the distal portion. Furthermore, since the hydrophilic lubricant layer 10 can cover the entire region of the tapered portion 62, the sliding property of the catheter is further improved. Therefore, with the hydrophilic lubricant layer 10 so disposed, it is possible to prevent the distal portion of the distal member 6 from being turned up and the catheter from being caught thereon. Accordingly, it is possible to obtain the guide wire 1 which exhibits excellent operability.

Next, a third exemplary embodiment of a guide wire of the disclosure will be described.

Figure 5:
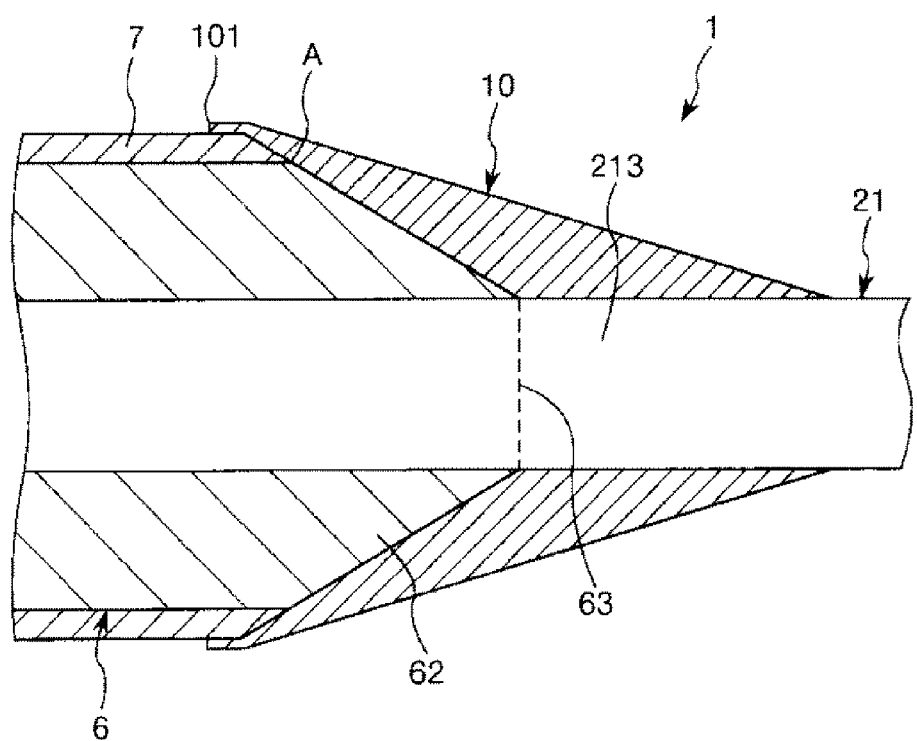
FIG. 5 is a partially enlarged vertical cross-sectional view illustrating a third exemplary embodiment of a guide wire of the disclosure.

FIG. 5 is a partially enlarged vertical cross-sectional view illustrating the third exemplary embodiment of the guide wire of the disclosure.

Hereinafter, the guide wire of the embodiment will be described. However, points different from those of the guide wire in the first exemplary embodiment will be mainly described. The same points will not be described.

The guide wire of the third embodiment is the same as the guide wire of the first embodiment except that the configurations of the hydrophilic lubricant layer are different from each other.

As illustrated in FIG. 5, in the third exemplary embodiment, the distal end 101 of the hydrophilic lubricant layer 10 is positioned at a further distal position than the tapered portion 62 of the distal member 6. That is, the hydrophilic lubricant layer 10 is formed to overlap with the entire region of the tapered portion 62 of the distal member 6, and further, the proximal portion of the distal side coating layer 7. As described above, this can improve the adhesion of the hydrophilic lubricant layer 10. In addition, since the hydrophilic lubricant layer 10 can cover the entire region of the tapered portion 62, the sliding property of the catheter is further improved. Furthermore, for example, there is no stepped portion formed due to different tapering angles between the outer peripheral surface of the tapered portion 62 and the outer peripheral surface of the hydrophilic lubricant layer 10 as in the first embodiment. Accordingly, the sliding property of the catheter is further improved. Therefore, with the hydrophilic lubricant layer 10 so disposed, it is possible to prevent the distal portion of the distal member 6 from being turned up and the catheter from being caught thereon. Accordingly, it is possible to obtain the guide wire 1 which exhibits excellent operability.

In addition, the hydrophilic lubricant layer 10 can cover a boundary A between the outwardly exposed distal member 6 and the distal side coating layer 7. Accordingly, it is possible to effectively prevent turning up of the distal side coating layer 7 from the distal member 6, which starts from the boundary A.

A fourth exemplary embodiment of a guide wire of the disclosure will be described below.

Figure 6:
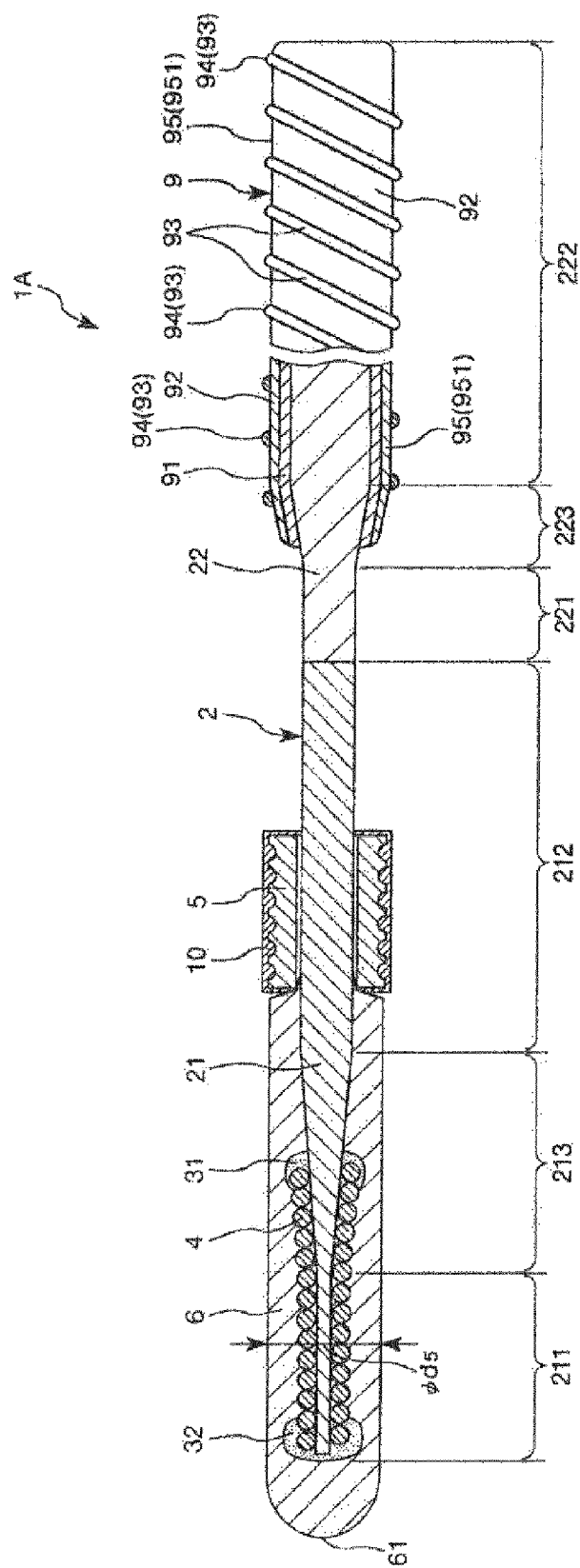
FIG. 6 is a vertical cross-sectional view illustrating a fourth exemplary embodiment of a guide wire of the disclosure.
Figure 7:
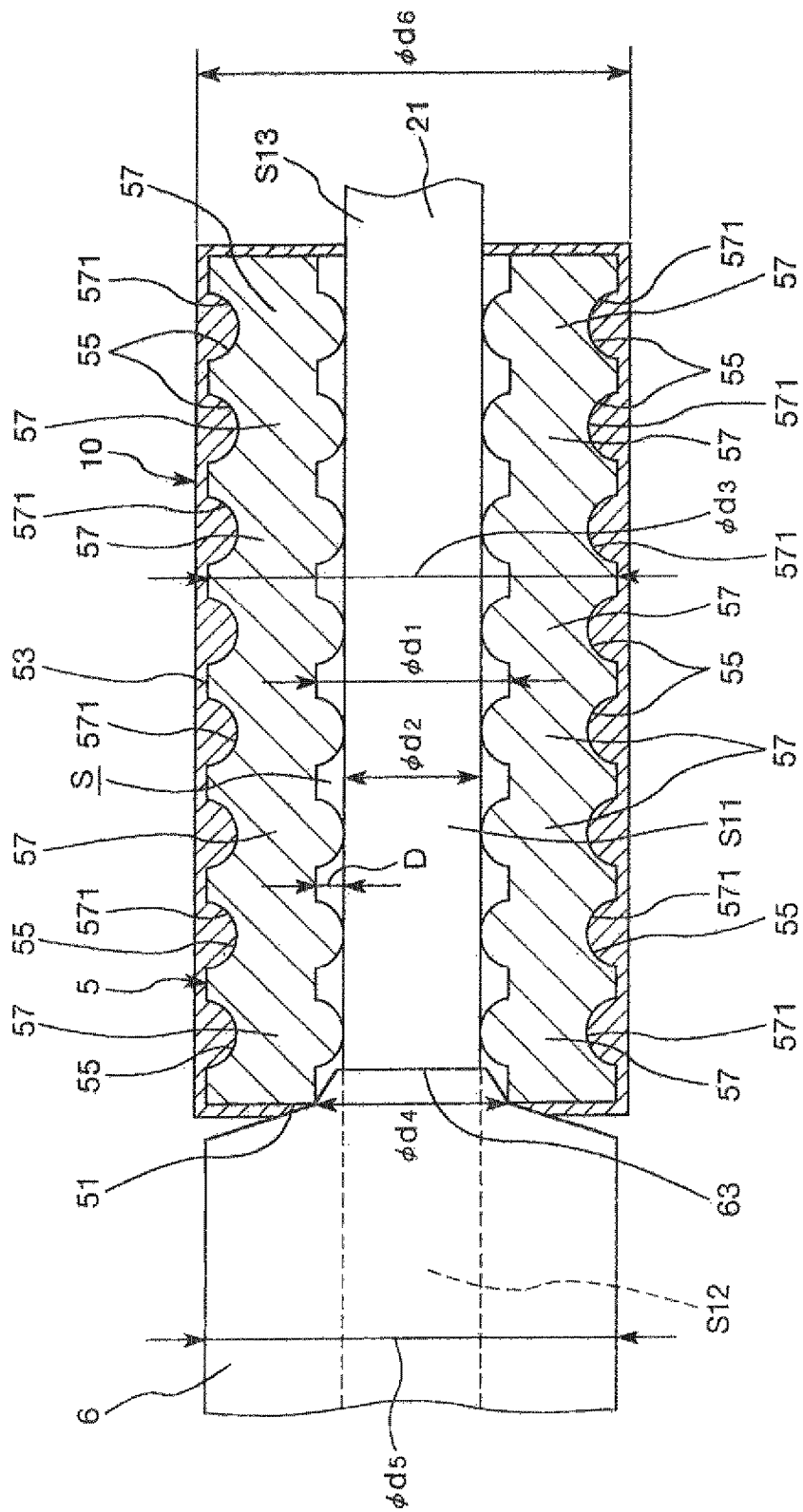
FIG. 7 is an enlarged cross-sectional view of a cylindrical member included in the guide wire illustrated in FIG. 6.
Figure 8:
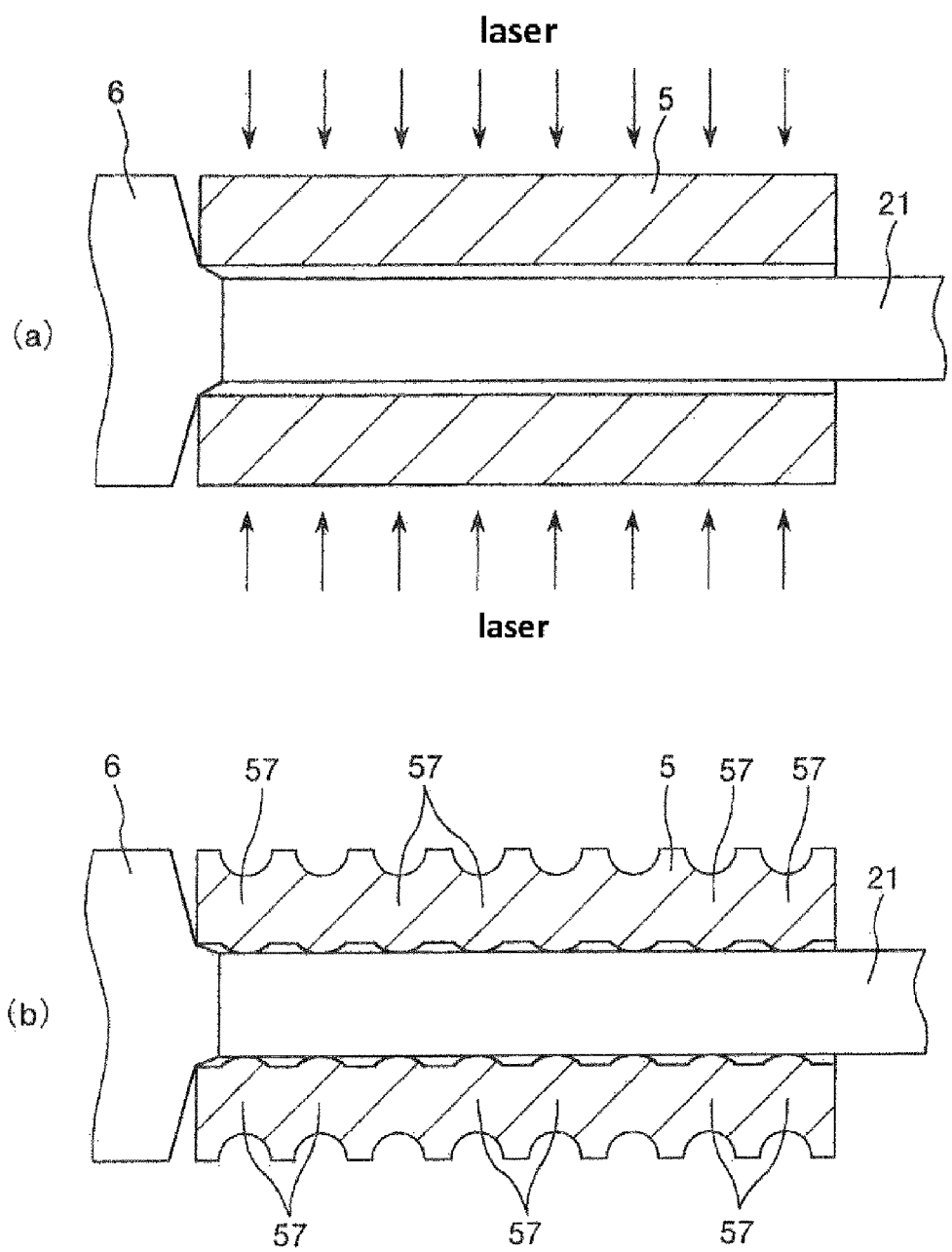
FIG. 8 is a cross-sectional view illustrating an example of a manufacturing method of the cylindrical member illustrated in FIG. 7.

FIG. 6 is a vertical cross-sectional view illustrating the fourth exemplary embodiment of the guide wire of the disclosure here. FIG. 7 is an enlarged cross-sectional view of a cylindrical member included in the guide wire illustrated in FIG. 6. FIG. 8 is a cross-sectional view illustrating an example of a manufacturing method of the cylindrical member illustrated in FIG. 7.

Hereinafter, the guide wire of the fourth exemplary embodiment will be described. However, points different from those of the guide wire in the first exemplary embodiment will be mainly described. The same points will not be described.

The guide wire of the fourth exemplary embodiment is the same as the guide wire of the first exemplary embodiment except that the distal side coating layer is omitted therefrom and the cylindrical member is added thereto.

A guide wire 1A illustrated in FIGS. 6 and 7 has the wire body 2, the coil 4, the distal member 6, a cylindrical member 5 disposed to protrude from the wire body 2, the hydrophilic lubricant layer 10 which coats the outer surface of the cylindrical member 5, and the coating layer 9. Among these, the wire body 2, the coil 4, the distal member 6 and the coating layer 9 have the same configurations as those of the aforementioned first exemplary embodiment. Accordingly, in the following description, the cylindrical member 5 and the hydrophilic lubricant layer 10 will be mainly described.

The cylindrical member 5 is configured to have a cylindrical (ring-shaped) configuration and is fixedly arranged in the second constant outer diameter portion 212 of the wire body 2 (first wire 21). In addition, the cylindrical member 5 is disposed so as to protrude outward from the wire body 2.

An inner diameter $\phi d1$ of the cylindrical member 5 is slightly larger than an outer diameter $\phi d2$ of the second constant outer diameter portion 212. That is, a relationship of $\phi d1 > \phi d2$ is satisfied, and a gap S is formed between the inner peripheral surface of the cylindrical member 5 and the outer peripheral surface of the second constant outer diameter portion 212. A thickness D of the gap S is not particularly limited, but it is preferable that the thickness D be approximately 5 μm to 30 μm. By adopting the thickness D of the gap S as described above, the gap S is decreased, and the first wire 21 and the cylindrical member 5 are increasingly integrated with each other, thereby improving the operability. In addition, the cylindrical member 5 is movable onto the wire body 2 in a state without being welded. Accordingly, it is possible to simply manufacture the guide wire 1 by using a manufacturing method to be described later.

In addition, a distal end 51 of the cylindrical member 5 is in contact with the distal member 6, and the proximal end 63 of the distal member 6 is inserted into the inner side (gap S) of the cylindrical member 5. In other words, the distal end 51 of the cylindrical member 5 is positioned at a further distal position than the proximal end 63 of the distal member 6. Therefore, the proximal end 63 of the distal member 6 is not exposed on the surface of the guide wire 1A (does not face outward from the guide wire 1A).

In addition, an outer diameter (maximum outer diameter) $\phi d3$ of the cylindrical member 5 is larger than an outer diameter $\phi d4$ of a portion where the distal end 51 of the cylindrical member 5 is positioned at the distal member 6. This cylindrical member 5 causes the proximal end 63 of the distal member 6 to be positioned further inside than the outer peripheral surface of the cylindrical member 5.

In addition, the outer diameter $\phi d3$ of the cylindrical member 5 is smaller than (or the same as) the maximum outer diameter $\phi d5$ of the distal member 6. The length of the cylindrical member 5 is shorter than the length of the distal member 6. Since there is a relationship of small and large sizes, for example, when the guide wire 1A moves inside the living body lumen, the distal member 6 having a better sliding property in the distal portion thereof comes into contact with a wall portion defining the living body lumen prior to the cylindrical member 5 coming into contact therewith. This enables the guide wire 1A to be operated without degrading the operability.

The length of the cylindrical member 5 is not particularly limited, but it is preferable that the length be approximately 0.5 mm to 2 mm. By adopting the above mentioned length, it is possible to set a sufficient length which enables the cylindrical member 5 to perform its function and can effectively prevent degradation in the operability of the guide wire 1A which would be caused by an excessively lengthened cylindrical member 5.

Moreover, a section S11 where the cylindrical member 5 of the wire body 2 is disposed has a rigidity higher than those of a section S12 of the distal side thereof and a section S13 of the proximal side. Accordingly, the section S11 is unlikely to be curved and deformed as compared to the section S12 and the section S13. If the section S11 which is unlikely to be curved is long, there is a possibility that the operability (in particular, the ability to follow) of the guide wire 1A may be degraded. Therefore, by arranging the cylindrical member 5 to have the above-described length and shortening as much as possible the section S11 which is unlikely to be curved and deformed, it is possible to effectively suppress the above-described degradation in the operability.

An unevenness is formed on an outer surface 53 of the cylindrical member 5. More particularly, the outer surface 53 of the cylindrical member 5 is configured to have an uneven surface. The uneven surface is obtained by forming a plurality of concave portions 55 on the flat outer surface 53. In this manner, by forming the unevenness on the outer surface 53, the adhesion between the cylindrical member 5 and the hydrophilic lubricant layer 10 is improved. Therefore, it is possible to suppress peeling of the hydrophilic lubricant layer 10 away from the cylindrical member 5. Each of the concave portions 55 is configured to have a curved and concave surface having a substantially circular contour. Note that, a shape of the concave portion 55 is not limited thereto, but for example, the contour may be a polygonal shape or the concave portion 55 may be configured to have a bent surface.

A depth (maximum depth) of the concave portion 55 is not particularly limited, but it is preferable that the depth be approximately 1 μm to 100 μm. In this manner, it is possible to form the unevenness having sufficient irregularities on the outer surface 53, thereby further improving the adhesion between the cylindrical member 5 and the hydrophilic lubricant layer 10.

The cylindrical member 5 has a plurality of melting portions 57 concavely deformed so as to protrude to the wire body 2 side by melting, and an external surface 571 of each of the melting portions 57 configures the concave portion 55. In addition, the melting portion 57 is configured so that an inner surface thereof is in pressurized contact with the wire body 2, thereby fixing the cylindrical member 5 to the wire body 2.

For example, the melting portion 57 can be formed by irradiating energy such as a laser from the outer peripheral side to the cylindrical member 5 and by melting the cylindrical member 5 to be thermally deformed. Specifically, for example, as illustrated in FIG. 8(a), the first wire which is not welded to the second wire 22 is first prepared, the cylindrical member 5 is inserted from the proximal side of the first wire 21, and the first wire is contacted with the proximal portion of the distal member 6. In this state, the cylindrical member 5 is slidable with respect to the first wire 21. Subsequently, the laser is emitted to multiple locations on the outer surface 53 of the cylindrical member 5 in a spot shape (island shape). Then, as illustrated in FIG. 8(b), the laser emitted portion is melted to be thermally and concavely deformed to the wire body 2 side. The melting portion 57 formed by the deformation is contacted with (is brought into pressurizing contact with) the wire body 2 with a pressure to some extent. This causes the cylindrical member 5 to be clamped to the wire body 2, thereby fixing the cylindrical member 5 to the wire body 2.

The melting portion 57 thus allows the cylindrical member 5 to be fixed to the wire body 2. Accordingly, it is possible to fix the cylindrical member 5 to the wire body 2 without using other members such as an adhesive or solder, for example. Therefore, it is simple to configure the guide wire 1A, thereby facilitating the manufacture of the guide wire 1A. In addition, for example, when fixing the cylindrical member 5 to the wire body 2 by using the aforementioned adhesive or solder, it is necessary to fill the gap S with the adhesive or the solder. Therefore, in order to fill the gap S with the adhesive or the solder, it is necessary to increase the thickness D of the gap S to some extent. This causes the cylindrical member 5 to be largely loosened from the wire body 2, thereby leading to a possibility of degraded operability. In contrast, in the guide wire 1A, the cylindrical member 5 is fixed thereto by using the melting portion 57. Accordingly, it is possible to set the thickness D of the gap S to be small, and thus, it is possible to effectively prevent occurrence of the aforesaid problem.

In addition, since the melting portion 57 is annealed by melting, a portion corresponding to the melting portion 57 of the cylindrical member 5 has a rigidity lower than the other portions. Therefore, as compared to a case which does not have the melting portion 57, the overall rigidity of the cylindrical member 5 becomes lower, thereby enabling the cylindrical member 5 to be easily curved.

Further, it is preferable not to weld the melting portion 57 to the wire body 2. That is, it is preferable that the melting portion 57 and the wire body 2 not be integrated with each other by welding. This decreases thermal damage to the wire body 2, and thus it is possible to configure the guide wire 1A to have excellent operability and reliability.

Moreover, it is preferable that the plurality of melting portions 57 (concave portions 55) be uniformly formed over the entire region of outer surface of the cylindrical member 5. This allows the cylindrical member 5 and the wire body 2 to be in an entirely uniformly joined state, thereby improving the operability of the guide wire 1A. Specifically, it is possible to maintain a state where a central axis of the wire body 2 and a central axis of the cylindrical member 5 are substantially coincident with each other, even if the wire body 2 is in a curved state, thereby improving the operability of the guide wire 1A. In addition to this, it is possible to further improve the adhesion between the hydrophilic lubricant layer 10 and the cylindrical member 5.

The plurality of melting portions 57 may be configured so that adjacent melting portions are separated from each other or are in contact with each other (partially overlapped with each other). In addition, shapes and sizes of the plurality of the melting portions 57 may be the same as each other, or may be different from each other. In addition, the plurality of the melting portions 57 may be regularly formed, or may be irregularly formed. In addition, the melting portions 57 may not be formed to spread over the entire region of the outer surface of the cylindrical member 5. For example, the melting portions 57 may be formed in any one region of the proximal portion, the central portion and the distal portion, or in any two regions selected from these three regions.

It is preferable that the cylindrical member 5 be formed to have a material harder than the resin material forming the distal member 6, and it is preferable to use a metal material as the material of the cylindrical member 5. For example, the metal material includes stainless steel, super-elastic alloys, cobalt-based alloys, and precious metals such as gold, platinum, tungsten and the like, or alloys containing these materials (for example, platinum-iridium alloy). In particular, it is preferable to use the platinum-iridium alloy in a viewpoint of the hardness and the processing workability.

Since the cylindrical member 5 is disposed as described above, the distal portion of the catheter is prevented from coming into contact with the proximal end 63 of the distal member 6 while the distal portion crosses over the cylindrical member 5 and is attached to the distal member 6. As a result, even though the proximal end 63 is slightly turned up, the distal portion of the catheter is reliably prevented from being caught on the proximal end 63.

Note that, in this exemplary embodiment, a case where the concave portion 55 is formed by using the melting portion 57 has been described, but a forming method of the concave portion 55 is not particularly limited thereto. For example, the concave portion 55 may be formed by partially removing the outer surface of the cylindrical member 5 using various etching methods, may be formed by applying stress from the outer peripheral side to partially deform the outer surface 53, or may be formed by forming a hole on the outer peripheral surface by using a drill.

The hydrophilic lubricant layer 10 is formed on the outer surface of the above-described cylindrical member 5 so as to cover the cylindrical member 5. Since the outer surface 53 of the cylindrical member 5 is configured to have the uneven surface, it is possible to ensure a wide contact area between the hydrophilic lubricant layer 10 and the cylindrical member 5, thereby improving the adhesion therebetween. In addition, the hydrophilic lubricant layer 10 is inserted into the concave portion 55. Accordingly, an anchor effect leads to the improved adhesion between the hydrophilic lubricant layer 10 and the cylindrical member 5, and can prevent peeling of the hydrophilic lubricant layer 10 away from the cylindrical member 5.

The outer surface of the hydrophilic lubricant layer 10 is configured to have a flat surface. In addition, the thickness of the hydrophilic lubricant layer 10 (thickness of a portion excluding the portion inserted into the concave portion 55, in other words, [an outer diameter $\phi d6$ of the hydrophilic lubricant layer 10]-[the outer diameter $\phi d3$ of the cylindrical member]) is not particularly limited, but it is preferable that the thickness be approximately 2 μm to 20 μm.

Note that, in this exemplary embodiment, the hydrophilic lubricant layer 10 is formed so as to cover the outer surface 53, the distal surface and the proximal surface of the cylindrical member 5. However, without being limited thereto, the hydrophilic lubricant layer 10 may be formed so as to cover only the outer surface 53 and to expose the distal surface and the proximal surface.

A fifth exemplary embodiment of a guide wire of the disclosure here will be described next.

Figure 9:
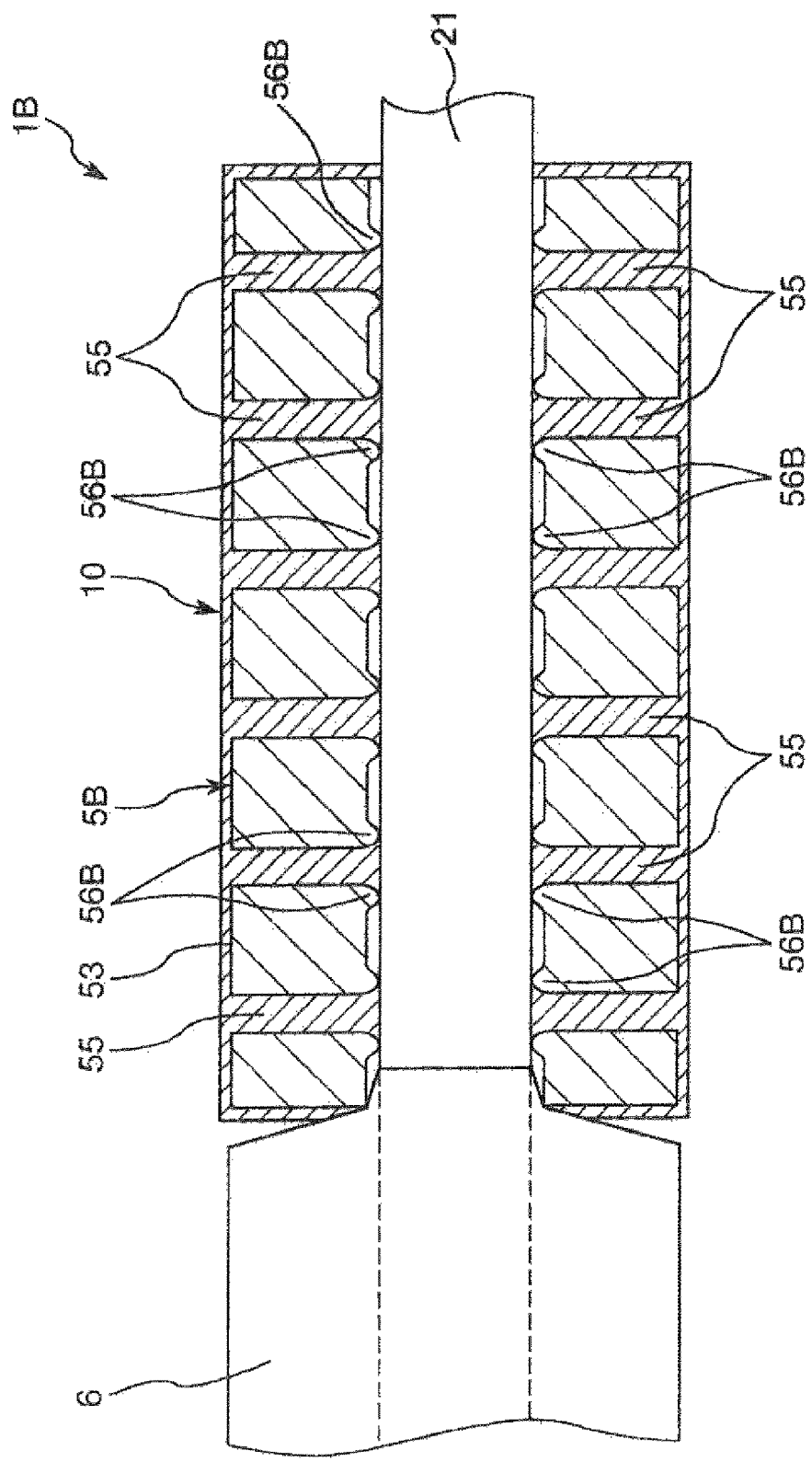
FIG. 9 is a cross-sectional view illustrating a cylindrical member included in a guide wire according to a fifth exemplary embodiment of the disclosure.

FIG. 9 is a cross-sectional view illustrating a cylindrical member included in the fifth exemplary embodiment of the guide wire of the disclosure.

Hereinafter, the guide wire of this exemplary embodiment will be described. However, points different from those of the guide wire in the fifth exemplary embodiment will be mainly described. The same points will not be described.

The guide wire of this exemplary embodiment is the same as the guide wire of the fourth exemplary embodiment except that a configuration of the cylindrical member is different.

As illustrated in FIG. 9, a plurality of concave portions 55 is formed on the outer surface 53 of a cylindrical member 5B included in a guide wire 1B of the fifth exemplary embodiment. In addition, each of the concave portions 55 is configured to have a through-hole penetrating an external surface (outer surface) and an inner surface of the cylindrical member.

A forming method of the concave portion 55 is not particularly limited. However, for example, similar to in the fourth embodiment, the concave portion 55 can be formed by emitting energy such as a laser from the outer peripheral side of the cylindrical member 5B. Specifically, for example, if the laser is emitted to the cylindrical member 5B for a time period longer than that of the case where the melting portion 57 is formed in the fourth embodiment, and/or the laser of high intensity is emitted to the cylindrical member 5B, the laser emitted portion melts and evaporates. In this manner, the through-hole is formed in the laser emitted portion and the concave portion 55 is formed. In addition, a protruding portion 56B which is thermally deformed by the melting is formed around the concave portion 55 (through-hole) and is brought into pressurizing contact with the wire body 2. This protruding portion 56B causes the cylindrical member 5B to be fixed to the wire body 2.

In this manner, it is possible to lighten the cylindrical member by configuring the through-hole to be included in the concave portion 55, and thus it is possible to further reduce the rigidity of the cylindrical member 5B. Therefore, it is possible to effectively suppress degradation in the operability of the guide wire 1B.

Next, a sixth exemplary embodiment of a guide wire of the disclosure herein will be described.

Figure 10:
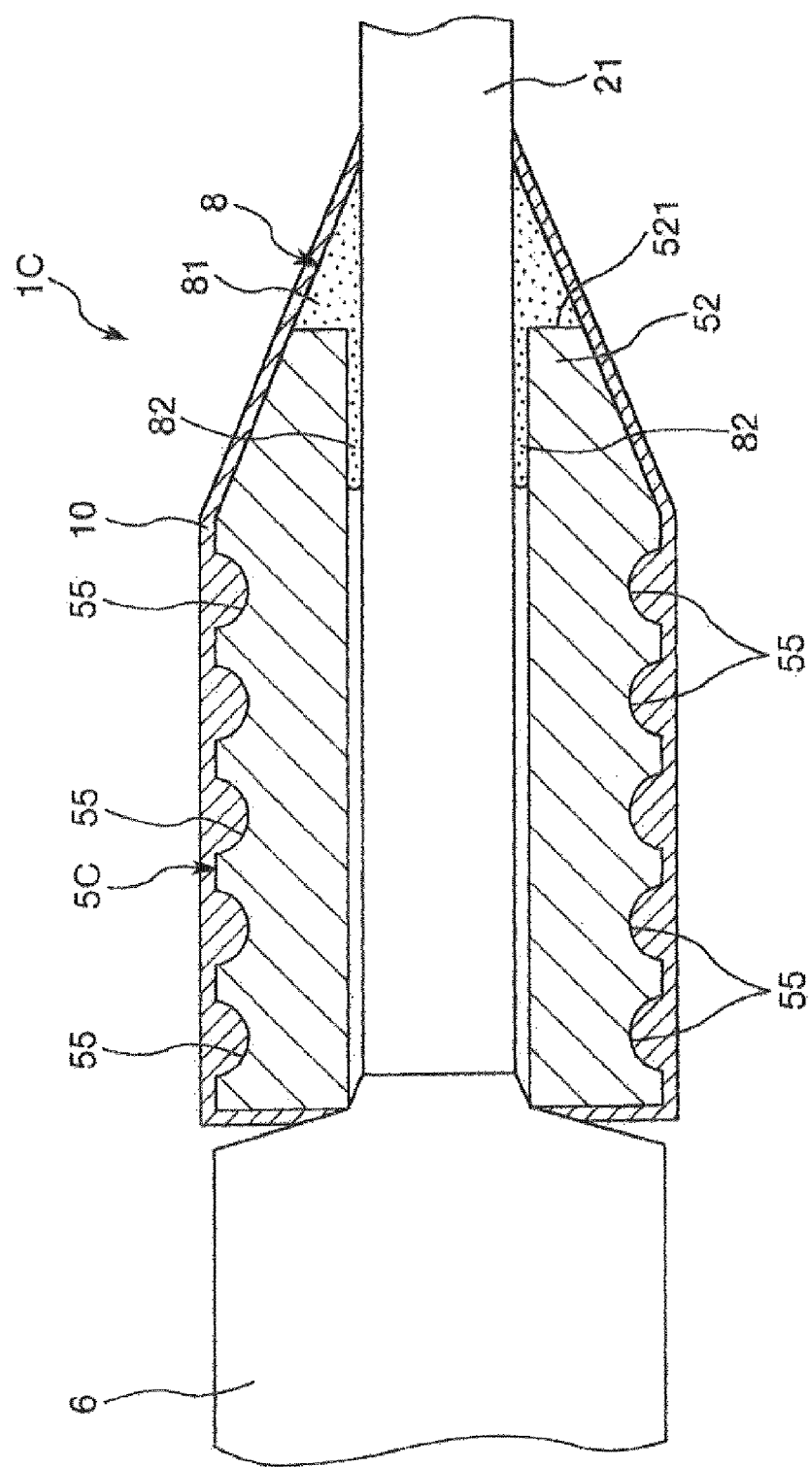
FIG. 10 is a cross-sectional view illustrating a cylindrical member included in a guide wire according to a sixth exemplary embodiment of the disclosure.

FIG. 10 is a cross-sectional view illustrating a cylindrical member included in the sixth embodiment of the guide wire of the disclosure.

Hereinafter, the guide wire of this exemplary embodiment will be described. However, points different from those of the guide wire in the fourth exemplary embodiment will be mainly described. The same points will not be described.

The guide wire of the sixth exemplary embodiment is the same as the guide wire of the fourth embodiment except that a configuration of the cylindrical member is different.

As illustrated in FIG. 10, a guide wire 1C of the sixth exemplary embodiment has a joining member 8 which joins (fixes) a cylindrical member 5C to the wire body 2.

The proximal portion of the cylindrical member 5C is configured to have the tapered portion 52 whose outer diameter gradually decreases toward the proximal direction. By thus arranging the tapered portion 52, it is possible to gradually change the rigidity (flexural rigidity, torsional rigidity) of the wire body 2 including the cylindrical member 5C toward the distal direction. In addition, it is possible to further minimize a difference in the rigidity between the distal side and the proximal side based on a boundary from the proximal end of the cylindrical member 5C. As a result, it is possible to improve the ability of the guide wire 1C to follow the blood vessels, and it is also possible to prevent the guide wire 1C from being bent.

In this exemplary embodiment, a tapering angle of the tapered portion 52 is substantially constant along the longitudinal direction. This enables the guide wire 1C to be more gradually changed in rigidity along the longitudinal direction. Note that, unlike in the above-described configuration, the tapering angle of the tapered portion 52 may be changed along the longitudinal direction, and for example, may be formed by alternately repeating a relatively large tapering angle portion and a relatively small tapering angle portion multiple times. In this case, there may be a portion where the tapering angle of the tapered portion 52 is zero degrees. Further, the cylindrical member 5C may not have the proximal portion configured to have the tapered portion 52, and for example, may have a constant outer diameter over the entire region in the longitudinal direction of the cylindrical member 5C.

The plurality of concave portions 55 is formed to spread over the entire region except for the tapered portion 52 of the cylindrical member 5C.

The joining member 8 is first used to join (fix) the cylindrical member 5C to the wire body 2. The joining member 8 has a base portion 81 positioned at the proximal side of the cylindrical member 5C and an extension portion 82 which extends from the base portion 81 and is inserted into the gap S. The base portion 81 is formed so as to come into contact with a proximal surface 521 of the cylindrical member 5C and the outer surface of the wire body 2. In this manner, the cylindrical member 5C is firmly joined to the wire body 2. The length of the base portion 81 is not particularly limited, but it is preferable that the length be approximately 0.5 mm to 2.0 mm.

On the other hand, the extension portion 82 extends from the base portion 81 and fills the proximal portion of the gap S. That is, the extension portion 82 is formed between the inner peripheral surface of the proximal portion of the cylindrical member 5C and the outer peripheral surface of the wire body 2. In this manner, the cylindrical member 5C is joined to the wire body 2. Further, the extension portion 82 may also be formed in the entire region of the gap S.

By disposing the base portion 81 and the extension portion 82 in this manner, a contact area is widened between the cylindrical member 5C and the wire body 2 via the joining member 8. Therefore, it is possible to more firmly join the cylindrical member 5C to the wire body 2.

Furthermore, the base portion 81 also functions as a step filling member which fills a step between the wire body 2 and the cylindrical member 5C. Specifically, the base portion 81 is positioned at the proximal side of the cylindrical member 5C, and has a tapered shape whose outer diameter gradually decreases toward the proximal direction. Therefore, the distal portion of the catheter is guided to the cylindrical member 5C along the outer peripheral surface of the base portion 81. As described above, the step between the wire body 2 and the cylindrical member 5C is filled with the base portion 81. In this manner, it is possible to prevent the catheter from being caught thereon. In addition, by causing the base portion 81 to have the tapered shape, it is possible to gradually change the rigidity of the wire body 2 including the base portion 81 toward the distal direction.

In particular, in this exemplary embodiment, the tapering angle of the base portion 81 is substantially equal to the tapering angle of the tapered portion 52 of the cylindrical member 5C, and the outer peripheral surface of the base portion 81 is continuously connected to the outer peripheral surface of the tapered portion 52 of the cylindrical member 5C. That is, regions in the vicinity of the proximal side and in the vicinity of the distal side are configured to have a flat surface having no step across the boundary between the base portion 81 and the cylindrical member 5C. Therefore, it is possible to effectively prevent the distal portion of the catheter from being caught on the boundary between the base portion 81 and the cylindrical member 5C.

It is preferable that the joining member 8 be configured to have a material softer than that of the cylindrical member 5C (material having a low Young's modulus). For example, it is possible to use various adhesives or solder as the material thereof. Out of these materials, it is preferable to use a solder which is relatively hard. This can thereby form the joining member 8 to have a high mechanical strength. In addition, it is possible to gradually change the rigidity of the wire body 2 including the joining member 8 and the cylindrical member 5C toward the distal direction.

The joining member 8 may be configured to have a material harder than that of the cylindrical member 5C (material having a high Young's modulus). In this case, the joining member 8 (in particular, the extension portion 82) also functions as a reinforcement member which reinforces the cylindrical member 5C. Therefore, for example, it is possible to lighten the cylindrical member 5C.

The hydrophilic lubricant layer 10 is formed so as to cover the outer surface of the cylindrical member 5C and the joining member 8 (base portion 81).

As set forth above, the illustrated exemplary embodiments of the guide wire of the disclosure have been described. However, the disclosure here is not limited thereto, and the respective elements configuring the guide wire can be replaced with any configuring element which can perform the same function. In addition, any configuring element may be added thereto. In addition, the guide wire of the disclosure herein may be made by arbitrarily combining two or more configuring elements (characteristics) out of the respective exemplary embodiments.

In addition, in the aforementioned exemplary embodiments, a case has been described in which the wire body is prepared by joining two wires together. However, the wire body may be configured to have only one wire or possibly more than two wires.

In addition, in the aforementioned exemplary embodiments, a case has been described in which the proximal end of the distal member is positioned in the middle of the second constant outer diameter portion of the first wire. However, the position of the proximal end of the distal member is not limited thereto. For example, the proximal end of the distal member may be positioned in the tapered portion of the first wire or in the middle of the first constant outer diameter portion, or may be positioned in the boundary between the tapered portion and the second constant outer diameter portion, or the boundary between the tapered portion and the second constant outer diameter portion.

In addition, in the aforementioned exemplary embodiments, a case has been described in which the cylindrical member is a circular tube type. However, for example, the cylindrical member may have a shape in which a slit for internally and externally communicating is formed in the entire region in the longitudinal direction thereof, that is, a C-shape in horizontal cross section.

In addition, in the aforementioned exemplary embodiments, a case has been described in which the gap is formed between the inner surface of the cylindrical member and the outer peripheral surface of the wire body. However, without being limited thereto, the gap may not be formed between the inner surface of the cylindrical member and the outer peripheral surface of the wire body. That is, the inner diameter of the cylindrical member may be equal to the outer diameter of the portion overlapped with the cylindrical member of the first wire.

A guide wire according to the present invention is characterized by including an elongated wire body 2 having flexibility; a distal member 6 that covers a distal portion of the wire body 2 and is configured to have a resin material; and a hydrophilic lubricant layer 10 that is formed so as to cover a proximal end of the distal member 6 and is configured to have a hydrophilic material. Therefore, when continuously pushing a medical device such as a catheter used in combination with the guide wire (referred to as a "catheter" as a representative example) to a target site of a living body lumen along the guide wire toward a distal direction, a distal portion of the catheter slides on the hydrophilic lubricant layer and is finally contacted with the middle of the distal member. When the catheter is moved as described above, even if external force is applied to a proximal end of the distal member by the distal portion of the catheter, the proximal end of the distal member is covered with the hydrophilic lubricant layer and is likely to slide on a proximal surface. Therefore, the force applied by the catheter dissipates and thus the proximal end of the distal member does not evolve into a turned-up shape. Accordingly, it is possible to reliably prevent the proximal end of the distal member from being turned up by the distal portion of the catheter being caught thereon.

The detailed description above describes a guide wire disclosed by way of example. The disclosure is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
an elongated wire body having flexibility;
a distal member that covers a distal portion of the wire body and is formed from a resin material;
a hydrophilic lubricant layer configured to cover a proximal end of the distal member and formed from a hydrophilic material;
at least a proximal portion of the hydrophilic lubricant layer possessing a tapered shape whose outer diameter gradually decreases toward a proximal side of the hydrophilic lubricant layer, a distal end of the hydrophilic lubricant layer being proximal to a distal end of the distal member; and
a maximum outer diameter of the hydrophilic lubricant layer being smaller than a maximum outer diameter of the distal member.

2. The guide wire according to claim 1,
wherein a proximal portion of the distal member has a tapered shape in which an outer diameter thereof gradually decreases toward a proximal side of the distal member, and
wherein the distal end of the hydrophilic lubricant layer is positioned at the tapered proximal portion of the distal member.

3. The guide wire according to claim 2,
wherein a tapering angle of the hydrophilic lubricant layer is smaller than a tapering angle of the tapered proximal portion of the distal member such that a distal portion the hydrophilic lubricant layer is positioned in a middle of the tapered proximal portion of the distal member.

4. The guide wire according to claim 1,
wherein the wire body has a first constant outer diameter portion which is positioned at a distal side and whose outer diameter is constant in a longitudinal direction, a second constant outer diameter portion which is positioned further towards a proximal side of the wire body than the first constant outer diameter portion and whose outer diameter is larger than the outer diameter of the first constant outer diameter portion and is constant in the longitudinal direction, and a tapered portion which is positioned between the first constant outer diameter portion and the second constant outer diameter portion and whose outer diameter gradually decreases toward the distal side, and
wherein a proximal end of the distal member is positioned at the second constant outer diameter portion.

5. The guide wire according to claim 1,
wherein the resin material comprises a urethane resin.

6. The guide wire according to claim 1, including a coating layer distally spaced from the hydrophilic lubricant layer.

7. A guide wire comprising:
an elongated wire body having flexibility;
a distal member that covers a distal portion of the wire body and is formed from a resin material;
a hydrophilic lubricant layer configured to cover a proximal end of the distal member and formed from a hydrophilic material; and
a maximum outer diameter of the hydrophilic lubricant layer being smaller than a maximum outer diameter of the distal member.

8. A guide wire comprising:
an elongated wire body having flexibility;
a distal member that covers a distal portion of the wire body and is formed from a resin material;
a hydrophilic lubricant layer configured to cover a proximal end of the distal member and formed from a hydrophilic material;
the wire body possessing a first constant outer diameter portion which is positioned at a distal side and whose outer diameter is constant in a longitudinal direction, a second constant outer diameter portion which is positioned further toward a proximal side of the wire body than the first constant outer diameter portion and whose outer diameter is larger than the outer diameter of the first constant outer diameter portion and is constant in the longitudinal direction, and a tapered portion which is positioned between the first constant outer diameter portion and the second constant outer diameter portion and whose outer diameter gradually decreases toward the distal side;
a proximal end of the distal member being positioned at the second constant outer diameter portion;
the distal member possessing a proximal end portion that is tapered and made of the same material as a remainder of the distal member, the hydrophilic lubricant layer directly contacting the tapered proximal end portion of the distal member; and
a maximum outer diameter of the hydrophilic lubricant layer being smaller than a maximum outer diameter of the distal member.

* * * * *